United States Patent [19]
Layton

[11] 4,205,690
[45] Jun. 3, 1980

[54] CATHETERIZATION DEVICE

[75] Inventor: Terry N. Layton, Arlington Heights, Ill.

[73] Assignee: The Kendall Company, Boston, Mass.

[21] Appl. No.: 955,450

[22] Filed: Oct. 27, 1978

[51] Int. Cl.² ............................................. A61B 10/00
[52] U.S. Cl. .................................... 128/768; 128/295
[58] Field of Search ............... 128/761, 766, 768, 295, 128/214 D, 214.4, 349, 350; 222/525, 522, 521; 73/425.6

[56] References Cited

U.S. PATENT DOCUMENTS

| | | | |
|---|---|---|---|
| 2,037,922 | 4/1936 | Punte | 222/525 |
| 3,547,401 | 12/1970 | Beall | 128/214 D |
| 3,888,235 | 6/1975 | May et al. | 128/761 |
| 3,991,617 | 11/1976 | Marteau d'Autry | 73/425.6 X |
| 4,020,981 | 5/1977 | Nixdorff | 222/525 |
| 4,055,179 | 10/1977 | Manschot et al. | 128/295 X |

*Primary Examiner*—Kyle L. Howell
*Attorney, Agent, or Firm*—Powell L. Sprunger

[57] ABSTRACT

A catheterization device comprising, a catheter having an elongated shaft defining a drainage lumen, a drainage eye adjacent a distal end of the shaft, and a proximal end. The device has a receptacle having a collection chamber, and a valve assembly communicating with the receptacle chamber and having a channel to receive the proximal end of the catheter. The valve assembly is movable between a first open position establishing communication between the receptacle chamber and the catheter lumen while the catheter is received in the channel, and a second closed position with the receptacle chamber closed from the channel. The valve assembly automatically substantially ejects the catheter from the channel responsive to movement of the valve assembly from the first to second position.

4 Claims, 5 Drawing Figures

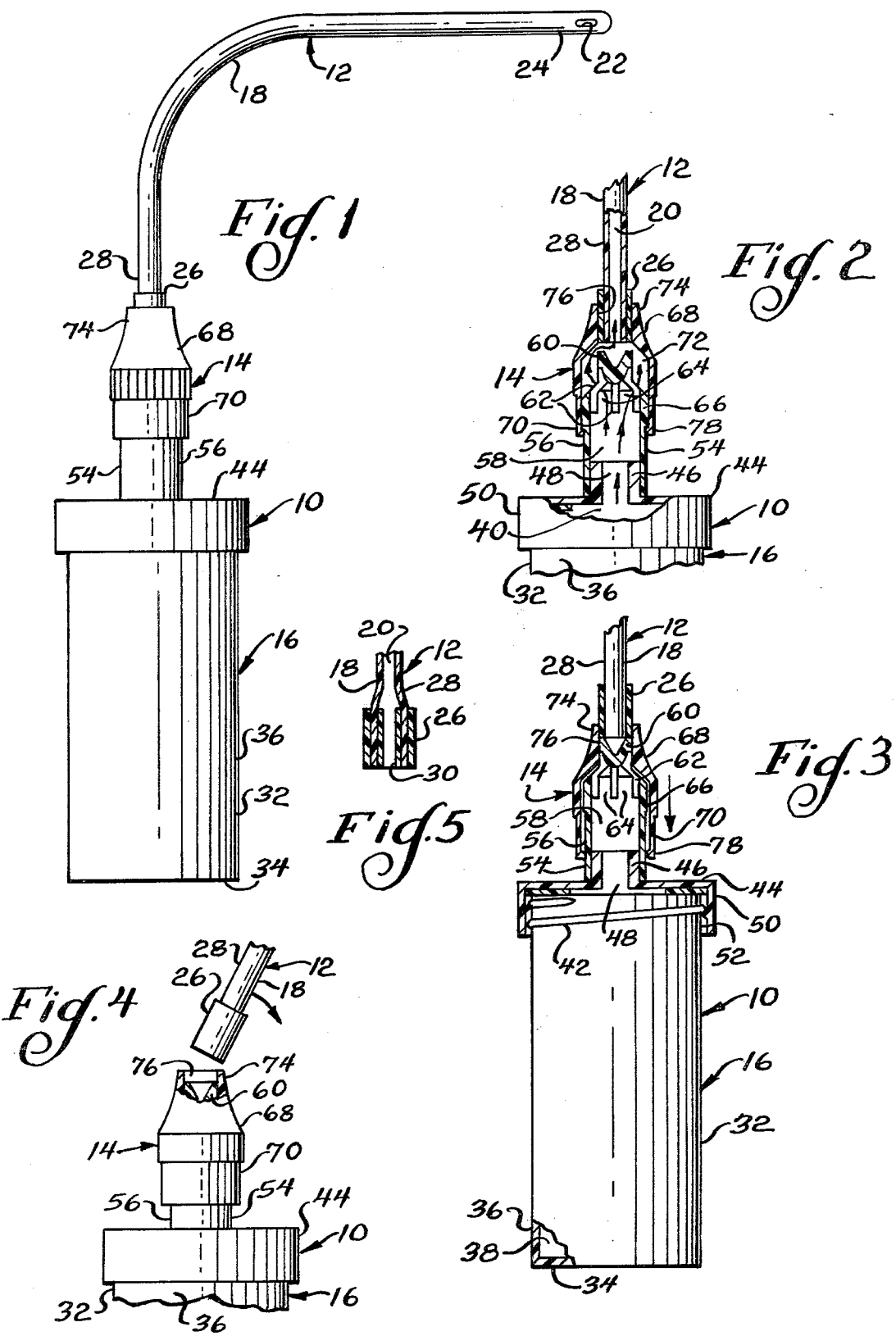

CATHETERIZATION DEVICE

BACKGROUND OF THE INVENTION

The present invention relates to drainage devices, and more particularly to catheterization systems.

A various assortment of catheterization systems have been proposed in the past for use in collecting urine from the bladder of a patient. In the usual case, the systems comprise a urinary or Foley catheter having an inflatable balloon and drainage eye adjacent a distal end of the catheter shaft, and a drainage lumen in the shaft communicating with the drainage eye. During placement, the catheter is passed through the urethra until the distal end of the catheter is located in the bladder, and the balloon is inflated to retain the catheter in place. During catheterization, urine drains through the catheter eye and lumen, and through a drainage tube to a collection bag for retention therein.

Although many such drainage systems have been found satisfactory, they are designed for use over prolonged periods of time. In many instances, however, it is desirable to temporarily catheterize a patient, particularly a female patient, in order to obtain an aseptic sample of urine for purposes of analysis. Hence, such specimen catheterization systems are utilized for a relatively short period of time, and should permit simplified placement and use by the physician without contamination of the urine specimen.

SUMMARY OF THE INVENTION

A principal feature of the present invention is the provision of a improved catheterization device of simplified construction.

The catheterization device of the present invention comprises, a catheter having an elongated shaft defining a drainage lumen, a drainage eye adjacent a distal end of the shaft, and a proximal end. The device has a receptacle having a collection chamber, and valve means communicating with the receptacle chamber and having means defining a channel to receive the proximal end of the catheter. The valve means is movable between a first open position establishing communication between the receptacle chamber and the catheter lumen, and a second closed position with the receptacle chamber closed from the channel.

A feature of the present invention is that the proximal end of the catheter may be placed in the channel of the valve means with the valve means in the open position.

Thus, a feature of the present invention is that the device permits simplified attachment of the catheter to the valve means with the catheter lumen in communication with the receptacle chamber through the valve means.

A further feature of the invention is that a patient may be catheterized with the catheter attached to the valve means and with the valve means in the open position in order that urine drains through the catheter and valve means to the receptacle chamber for collection therein.

Yet another feature of the invention is that after the urine specimen has been obtained the valve means may be moved to the closed position in order to close the collection chamber from the atmosphere.

Still another feature of the invention is that the valve means automatically substantially ejects the catheter from the channel responsive to movement of the valve means from the open to closed position.

Thus, a feature of the invention is that the device minimizes the possibility that the specimen may become contaminated during use of the device, and permits the sample to be obtained in a simplified manner.

Still another feature of the invention is that the device may be constructed from relatively inexpensive parts in order to reduce the cost of the device to the patient.

Further features will become more fully apparent in the following description of the embodiments of this invention and from the appended claims.

DESCRIPTION OF THE DRAWINGS

In the drawings:

FIG. 1 is an elevational view of a catheterization device of the present invention;

FIG. 2 is a fragmentary elevational view, taken partly in section, of the device of FIG. 1 illustrating a valve assembly of the device in an open configuration;

FIG. 3 is a fragmentary elevational view, taken partly in section, of the device of FIG. 1 illustrating the valve assembly in a closed configuration;

FIG. 4 is a fragmentary elevational view, taken partly in section, of the device of FIG. 3 illustrating removal of a catheter from the valve assembly; and FIG. 5 is a fragmentary view of another embodiment of the catheter for use in the device of FIG. 1.

DESCRIPTION OF THE PREFERRED EMBODIMENTS

Referring now to FIGS. 1–3, there is shown a catheterization device generally designated 10 having a catheter 12, a valve assembly 14, and a receptacle 16. The catheter 12 has an elongated shaft 18 defining a lumen 20 extending through the shaft, and at least one drainage eye 22 adjacent a distal end 24 of the shaft 18 communicating with the drainage lumen 20. The catheter 12 may be constructed from any suitable material, such as latex rubber or silicone. As shown in FIG. 2, the catheter 12 has an outer reinforcement member 26 comprising a cylindrical sleeve extending circumferentially around a proximal end 28 of the catheter shaft 18. In an alternative form, as shown in FIG. 5, the catheter 12 may have a second reinforcement member 30 comprising a circumferential sleeve extending around an inner surface of the catheter shaft 18 at the proximal end 28 thereof, with the second reinforcement member 30 having an inner diameter approximately equal to the inner diameter of the catheter lumen 20, and with the proximal end 28 of the shaft 18 being retained between the first and second reinforcement members 26 and 30.

With reference to FIGS. 1–3, the receptacle 16 comprises a container 32 having a lower wall 34 and sidewalls 36 defining a chamber 38. The upper portion of the container sidewalls 36 define an opening 40 communicating with the chamber 38, and has suitable threads 42 extending circumferentially around the upper portion of the sidewalls 36. The receptacle 16 also has a lid 44 having an upwardly extending tubular section 46 defining an opening 48, and a depending annular flange 50 having inner threads 52 which cooperate with the container threads 42 to releasably attach the lid 44 onto the container 32 and close the opening 40. The container 32 and lid 44 may be made from a suitable plastic material, and, in a preferred form, the container 32 is transparent.

The valve assembly 14 comprises an inner or first valve element 54 having a proximal cylindrical conduit 56 defining a passageway 58, a sealing or ejection head 60 of reduced external dimensions relative to the conduit 56 and located at the distal end of the inner valve element 54, and a plurality of spaced fingers 62 extending between the conduit 56 and sealing head 60 and defining a plurality of spaced openings 64. As shown, a proximal end of the conduit 56 is connected to the tubular section 46 with the passage 58 communicating with the opening 48 in the lid 44. Also, the conduit 56 has an outer shoulder 66 located adjacent the openings 64.

The valve assembly 14 also has an outer or second valve element 68 having a generally annular central section 70 defining a cavity 72 and tapering toward a distal end portion 74 which defines a channel 76 communicating with the cavity 72. The outer valve element 68 is slidably received on the inner valve element 54, and the outer valve element 68 has an inwardly directed annular flange 78 at the proximal end of the outer valve element 68, with the flange 78 being located proximal the shoulder 66 of the inner valve element 54, such that the flange 78 limits forward or distal movement of the outer valve element 68 relative to the inner valve element 54.

The valve assembly 14 is movable between a first open position, as shown in FIG. 2, and a second closed position, as shown in FIG. 3. With reference to FIG. 2, in the first open position of the valve assembly 14, the sealing head 60 is spaced from the channel 76 of the distal end portion 74, such that communication is established between the passageway 58 and the cavity 72 through the openings 64. Also, in this configuration, the proximal end 28 of the catheter 12 is received in the channel 76 of the valve assembly 14, with the reinforcement member 26 sealingly engaging against the inner surface of the distal end portion 74. Thus, in the first open position, the valve assembly 14 establishes communication between the receptacle chamber 38 and the catheter lumen 20 through the passageway 58, openings 64, and cavity 72, such that urine is permitted to drain from the catheter 12 through the valve assembly 14 into the receptacle chamber 38 during catheterization.

With reference to FIG. 3, in the closed second position of the valve assembly 14, the sealing head 60 is received in the channel 76, and sealingly engages against the inner surface of the distal end portion 74 in the channel 76, in order to close the valve assembly and the container chamber 38 from the atmosphere. Further, as shown, the distal end of the sealing head 60 engages against the proximal end 28 of the catheter 12, such that the sealing head 60 substantially ejects the catheter from the valve assembly channel 76 responsive to movement of the valve assembly from its open to closed position.

In use, with reference to FIGS. 1–3, the outer valve element 68 is moved distally relative to the inner valve element 54 in order to place the valve asembly 14 in its first open position, and the proximal end 28 of the catheter 12 is inserted into the valve assembly channel 76. Next, the catheter 12 is passed through the urethra of a patient, particularly a female patient, until the distal end 24 of the catheter 12 is located in the patient's bladder, such that urine drains through the eye 22, the drainage lumen 20, and the open valve assembly 14 into the receptacle chamber 38 for collection therein. After a sufficient sample has been collected, the catheter 12 may be removed from the patient, and the outer valve element 68 may be moved proximally relative to the inner valve element 54 in order to close the valve assembly 14. At the same time, the valve assembly automatically substantially ejects the catheter responsive to closure of the valve assembly, such that the catheter 12 may be readily removed from the valve assembly 14, as shown in FIG. 4.

Thus, in accordance with the present invention, the device permits catheterization in a simplified manner in order to obtain a sample of urine. Further, the device automatically ejects the catheter responsive to closure of the valve assembly, such that the device may be manipulated in a simplified manner while minimizing the possibility of contamination of the sample. After closure of the valve assembly, the receptacle may be shipped to the laboratory and stored until ready for use, after which the lid 44 may be removed from the container 32 in order to gain access to the aseptic urine sample for purposes of analysus.

The foregoing detailed description is given for clearness of understanding only, and no unnecessary limitations should be understood therefrom, as modifications will be obvious to those skilled in the art.

I claim:

1. A catheterization device, comprising
    a catheter having an elongated shaft with a drainage lumen, a drainage eye adjacent the distal end of said shaft, and a proximal end
    a receptacle having a collection chamber, and
    a slide valve assembly comprising
    an inner valve element mounted on said receptacle extending upwardly therefrom, said inner valve element having a lower portion with an internal passageway communicating with said receptacle collection chamber, an upper sealing and ejection portion of reduced external dimension relative to said lower portion external dimension and an intermediate portion having opening means extending therethrough to said passageway
    an outer valve element having a lower portion slideably mounted on the lower external portion of said inner valve element, an intermediate portion having its internal portion communicating with said inner valve element opening means and an upper portion of reduced internal dimension defining a channel slideably and sealably receiving at its distal end the proximal end of said catheter therewithin and at its proximal end the outer surface of said upper portion of said inner valve element into adjacent abutting position with said proximal end of catheter,
    said outer valve element being axially moveable along said inner valve element between
    an open valve position with said upper sealing portion of said inner valve element downwardly axially spaced from outer valve element channel for fluid communication between said catheter lumen and said receptacle through said opening means and said passageway and
    a closed valve position with said upper sealing portion of said inner valve element sealingly received within said outer valve element channel to close said container chamber from the atmosphere and abutting said proximal end of said catheter to substantially eject said catheter from said channel.

2. A catheterization device as claimed in claim 1, wherein
    said inner valve element has external stop means adjacent the upper end thereof
    said outer valve element has internal stop means adjacent the lower end thereof and said inner and outer valve element stop means are in contact with one another in said open valve position.

3. A catherization device as claimed in claims 1 or 2, wherein
said receptacle comprises
a container having walls defining said chamber and an opening at an upper portion of said container communicating with said chamber, a lid for closing the container opening and means for releasably attaching said lid to said container to close said opening.

4. A catherization device as claimed in claim 3, wherein
said inner valve element is mounted on said lid.